United States Patent [19]

May et al.

[11] Patent Number: 5,002,574
[45] Date of Patent: Mar. 26, 1991

[54] TENSIONING MEANS FOR PROSTHETIC DEVICES

[75] Inventors: Steven J. May; Craig L. Van Kampen, both of St. Paul, Minn.; David L. Butler, Fairfield Oh.; Edward S. Grood, Cincinnati, Oh.; Steven D. Hoffman, Cold Spring, Ky.; Frank R. Noyes, Cincinnati, Oh.

[73] Assignee: Minnesota Mining and Manufacturing Co., St. Paul, Minn.

[21] Appl. No.: 395,470

[22] Filed: Aug. 18, 1989

[51] Int. Cl.⁵ .................................................. A61F 2/08
[52] U.S. Cl. ........................................ 623/13; 623/16
[58] Field of Search ................ 606/72, 73, 75; 623/13, 623/16

[56] References Cited

U.S. PATENT DOCUMENTS

| | | |
|---|---|---|
| 3,896,500 | 7/1975 | Rambert et al. . |
| 3,953,896 | 5/1976 | Treace . |
| 4,246,660 | 1/1981 | Wevers ................... 623/13 |
| 4,301,551 | 11/1981 | Dore et al. . |
| 4,345,339 | 8/1982 | Muller et al. . |
| 4,712,542 | 12/1987 | Daniel et al. ................ 623/13 |
| 4,744,793 | 5/1988 | Parr et al. . |
| 4,772,286 | 9/1988 | Goble et al. ................ 623/13 |
| 4,776,851 | 10/1988 | Bruchman et al. ................ 623/13 |
| 4,828,562 | 5/1989 | Kenna ................... 623/13 |
| 4,940,467 | 7/1990 | Tronzo ................... 606/66 |
| 4,955,910 | 9/1990 | Bolesky ................... 623/13 |

FOREIGN PATENT DOCUMENTS

| | | | |
|---|---|---|---|
| 0232049 | 8/1987 | European Pat. Off. ............ 623/13 |
| 1419690 | 8/1988 | U.S.S.R. ................... 606/72 |
| 1475628 | 4/1989 | U.S.S.R. ................... 606/73 |

Primary Examiner—Randall L. Green
Assistant Examiner—David H. Willse
Attorney, Agent, or Firm—Donald M. Sell; Walter N. Kirn; Carolyn A. Bates

[57] ABSTRACT

This invention provides improved prosthetic devices for the replacement of a ligament or a tendon. The tension borne by the prosthetic ligament or tendon can be readily increased or decreased without disturbing the attachment of the device to bone and without removal of the prosthetic ligament or tendon from the other components of the device.

17 Claims, 4 Drawing Sheets

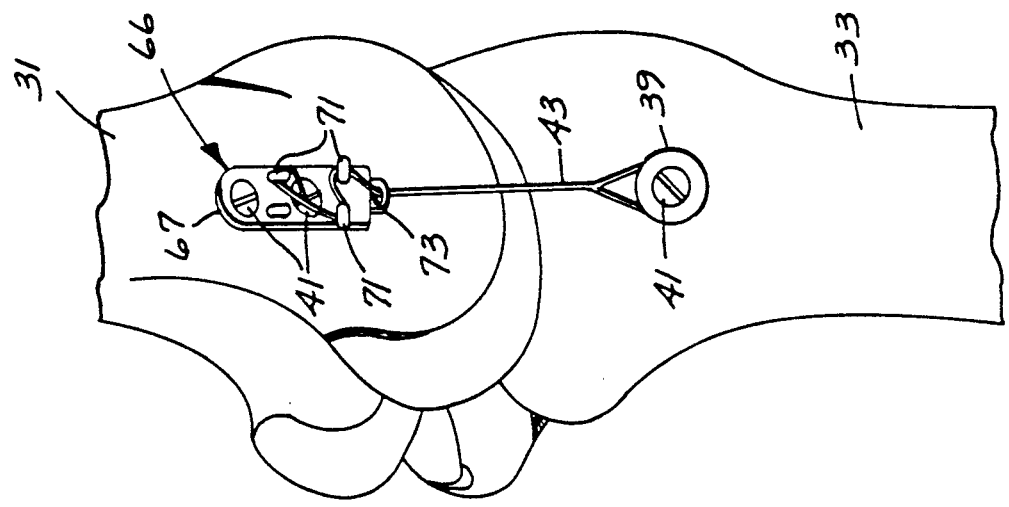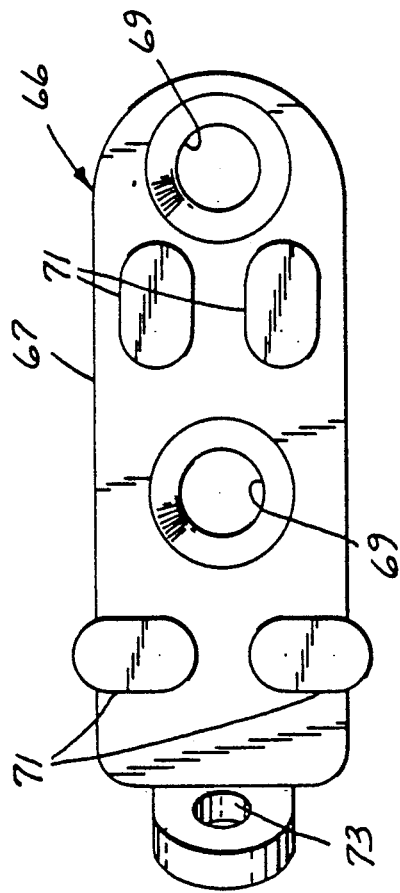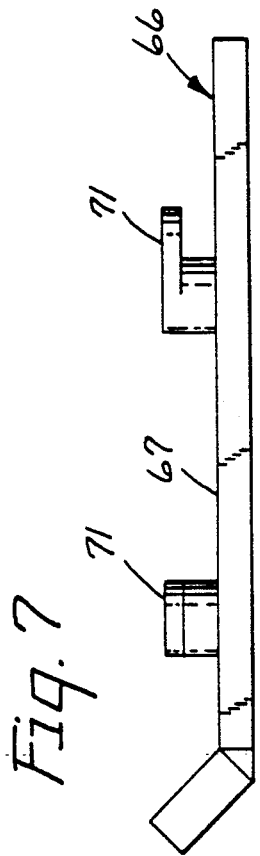

TENSIONING MEANS FOR PROSTHETIC DEVICES

BACKGROUND OF THE INVENTION

1. Technical Field

This invention relates to prosthetic devices for the replacement of a tendon or a ligament.

2. Description of the Related Art

The structural integrity of movable joints within the body is provided by tough strands of connective tissue known as ligaments. If these structures are severely damaged through injury, surgical replacement by a prosthesis may be indicated. Biomaterials that have been used as artificial ligaments (e.g., U.S. Pat. No. 4,411,827 for a resorbable version, U.S. Pat. No. 4,209,859 for a permanent version.), methods of attaching prostheses (e.g., U.S. Pat. No. 4,246,660) and suitable surgical techniques have all been described, and such replacements are now considered routine surgical procedures.

Current surgical technique requires that the tension on the ligament be properly adjusted during the procedure. Undertensioning the prosthesis compromises the stability of the joint, whereas overtensioning restricts the range of movement of the joint and may damage the soft tissues on the abutting surfaces. Unfortunately, achieving the proper adjustment depends in large part on the skill of the surgeon. Little in the way of mechanical aids is available to assist in achieving the proper balance of force. One mechanical aid in tensioning a prosthetic ligament is disclosed in U.S. Pat. No. 4,712,542. Here, a prosthetic ligament is attached to one fixation site and extended to the other fixation site, where it is attached to a tension-sensing device. Tension on the prosthesis is adjusted until a predetermined tension is achieved throughout the range of motion of the joint.

The patent literature describes several methods of adjusting a prosthetic ligament, but such adjustment methods generally involve loosening or otherwise adjusting a bone screw or like device which has an interface with the bone. It is well known that repeated movement of such devices that contact the bone causes additional trauma and compromises the strength of the bone.

A device of this nature is disclosed in U.S. Pat. No. 4,246,660. This device comprises an adjustable connector with an upper plate connected to the prosthesis and a base plate connected to the bone. The plates have complementary toothed surfaces which can be made to mesh at the point where the prosthetic ligament is at the proper tension. Adjustment of tension, however, involves loosening a bone screw which passes through both plates and into the bone.

Described in U.S. Pat. No. 3,953,896 is a prosthetic ligament wherein both ends are capable of adjustment. The ends are threaded and adapted to engage complementary female threads in conical fastening end members. These end members in turn are adapted to engage conical bores in the bone. Adjustment is accomplished through turning the end members on the threaded ligament and subsequent fixing with bone cement.

A like device is described in U.S. Pat. No. 4,744,793. Here both ends of the prosthetic ligament are tubular, and the conical bores in the bone are fitted with conical hollow anchor plugs. The ligament is placed through the anchor plugs and fixed at one end with a locking plug, which is pressed into the tubular end portion of the prosthesis causing a friction fit between the prosthesis and the anchor plug. The other end of the prosthesis is then pulled to the desired tension and similarly fixed with a locking plug. Any readjustment of tension requires release of fixation of the prosthesis.

A device described in U.S. Pat. No. 3,896,500 addresses the adjustability problem by providing an anchor plate with teeth directed such that the artificial ligament may be pulled tighter without disturbing the fixation to bone. However, adjustment in this device is only one-way and no provision is made for loosening the ligament in the event of over-tensioning.

SUMMARY OF THE INVENTION

The present invention provides an improved prosthetic device for the replacement of a ligament or a tendon. The above cited limitations in the prior art are ameliorated by a device whereby the tension borne by the prosthetic ligament or tendon can be readily increased or decreased without disturbing the attachment of the device to the bone and without removal of the prosthetic ligament or tendon from the other components of the device. Generally stated, the device of the invention comprises three parts. First, a prosthetic ligament, being both flexible and capable of sustaining significant tensile loads. Second, a fixed connector, adapted to be attached to living bone and adapted to engage the prosthetic ligament. Third, an adjustable connector, also adapted to be attached to living bone and also adapted to engage the prosthetic ligament.

When in use, the fixed connector and the adjustable connector are attached to different bones on opposite sides of an injured joint. Attachment can be by any suitable means, for example, adhesives, bone screws and like means that can afford solid attachment of the connectors to bone and thus prevent movement of the connectors at the bone-connector interface. The prosthetic ligament is positioned between the two connectors and engaged with both in order to provide the desired function of the ligament. A salient feature of the invention is that adjustment of the adjustable connector can increase or decrease the tension on the prosthetic ligament without disturbing the attachment of either of the connectors of the device to the bone and without removal of the prosthetic ligament from either of the connectors.

Three preferred embodiments of the adjustable connector for use in a device of the invention are described below. The first of these comprises an anchor adapted to be attached to living bone. This anchor has walls defining a socket, and this socket is designed to engage a pin with a rounded head that fits into the socket. This pin has a shaft, the end of which is threaded. A cylinder having a body with a threaded bore therein is provided, such that the threaded end of the pin engages the threads in the cylinder. One end of the cylinder has means, such as a hook-like member, or preferably a ring, for engaging the prosthetic ligament.

The second preferred embodiment of the adjustable connector comprises a spool having a ratchet plate attached and having means for engaging the prosthetic ligament. An attachment plate adapted to be attached to living bone is provided, and this attachment plate has a mating surface adapted to engage the ratchet plate on the spool. Fastening means are provided for fastening the spool to the attachment plate, which means can be either partially or fully engaged. When the fastening means are partially engaged, the spool is capable of being rotated to adjust the tension on the prosthetic ligament. When the surgeon determines that the tension is correct, the fastening means are fully engaged, and in that condition, the spool cannot rotate to change the selected tension.

The third preferred embodiment of the adjustable connector comprises a cleat plate adapted to be attached to living bone. This cleat plate has a plurality of cleats on its surface, these cleats being adapted to engage the prosthetic ligament. Typically the end of the prosthetic ligament will have a loop that slips over the top of a cleat. When the connector is properly constructed, there exist a plurality of routes around these cleats leading to a point of engagement of the prosthetic ligament with the connector. By choosing how to route the prosthetic ligament around the cleats, the surgeon can choose very closely the exact amount of tension applied because each route has a different path length and draws in the prosthetic ligament to a different degree.

BRIEF DESCRIPTION OF THE DRAWINGS

A more complete understanding of the invention and its advantages will be apparent from the accompanying drawing, in which:

FIG. 6 is a top view of an adjustable connector for use in a device of the present invention, wherein the adjustable aspect arises from a cleat plate with multiple cleats for variable engagement with the prosthetic ligament.

FIG. 7 is a side view of the adjustable connector illustrated in FIG. 6.

FIG. 8 is a side view of a human knee joint showing a device of the invention comprising a fixed connector and the adjustable connector illustrated in FIG. 6 in place with a prosthetic ligament attached, thus forming a prosthesis for a collateral ligament.

DETAILED DESCRIPTION OF THE PREFERRED EMBODIMENTS

Figure 1:
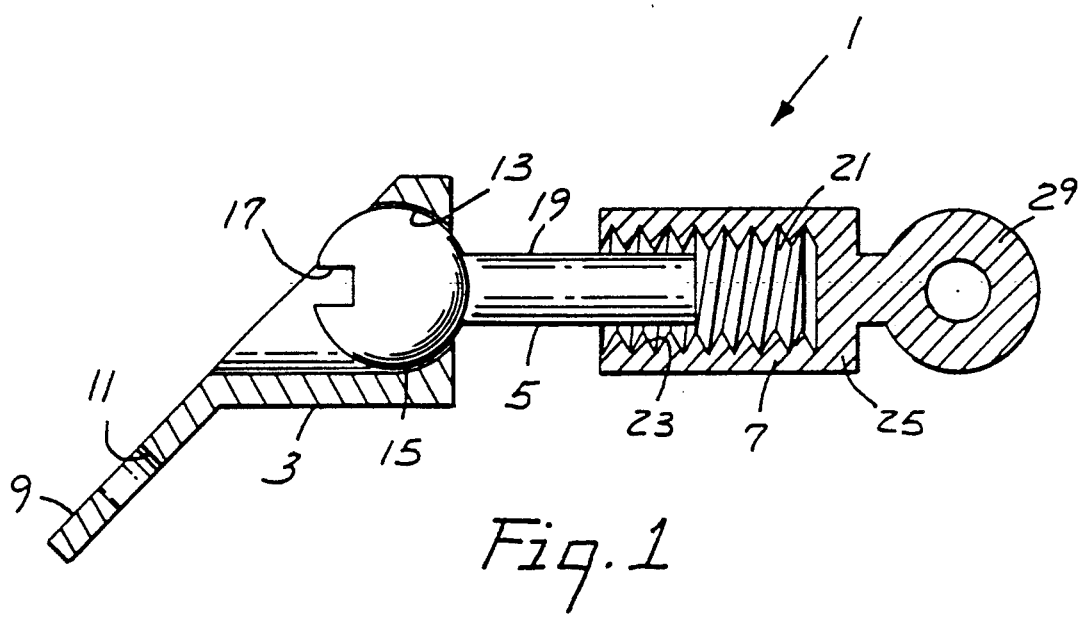
FIG. 1 is a cross-sectional view of an adjustable connector for use in a device of the present invention, wherein the adjustable aspect arises from a threaded pin engaging a threaded cylinder.

Referring to FIG. 1, a cross-sectional view of an adjustable connector for use in a device of the present invention is shown. Adjustable connector 1 comprises anchor 3, pin 5, and cylinder 7. Anchor 3 has flange 9 with screw hole 11, which allows anchor 3 to be attached to living bone. Anchor 3 also has socket 13 with rounded inner walls that match the curvature of rounded head 15 of pin 5. The rounded walls serve to permit a ready swivel movement of pin 5 within socket 13.

The axially adjustable member of this embodiment consists of threaded pin 5 and cylinder 7 with a complementary threaded bore. Rounded head 15 of pin 5 is accessible and has slot 17 which allows a tool such as a screwdriver, socket wrench, or the like to be inserted to facilitate adjustment of adjustable connector 1. Pin 5 also has shaft 19 and threaded end 21 which engages complementary threaded bore 23 of cylinder 7, allowing the position of the pin within the threaded bore to be adjusted by relative rotation of the pin and the cylinder.

Figure 2:
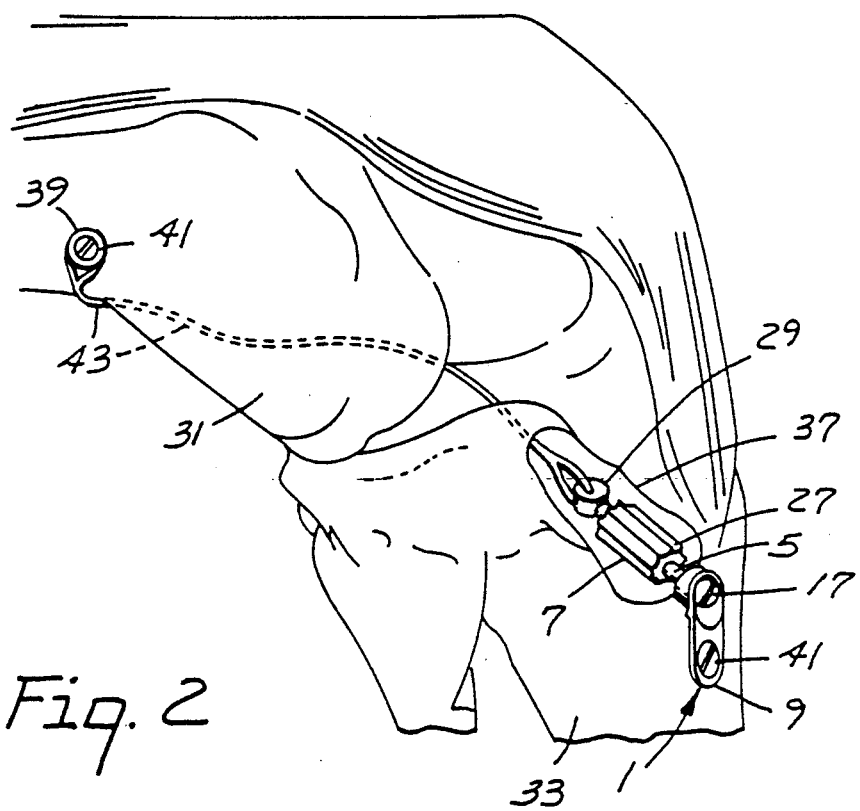
FIG. 2 is a quarter side view of a human knee joint showing a device of the invention comprising a fixed connector and the adjustable connector illustrated in FIG. 1 in place with a prosthetic ligament attached, thus forming a prosthesis for an anterior cruciate ligament.

Cylinder 7 has body 25 with threaded bore 23 therein, and bears flutes 27 (as shown in FIG. 2) on its outer surface. Flutes 27 prevent cylinder 7 from turning within the bone tunnel in which it is placed during surgery, insuring that any rotation of pin 5 is translated into axial adjustment of pin 5 within threaded bore 23. Cylinder 7 also has ring 29 at the end opposite threaded bore 23 which ring 29 is adapted to engage the prosthetic ligament. When the other end of the prosthetic ligament is engaged, rotation of pin 5 allows adjustment of tension on the prosthetic ligament without twisting the prosthetic ligament and, as in all embodiments of the invention, without its removal from either of the connectors.

FIG. 2 is a quarter side view of a human knee joint showing a device of the invention comprising a fixed connector and the adjustable connector of FIG. 1 in place with a prosthetic ligament engaged with both, thus forming a prosthesis for an anterior cruciate ligament. In this view a portion of the tibia is shown sectioned so that the cylinder is seen within a bone tunnel. For illustrative purposes, anchor 3 of adjustable connector 1 in FIG. 2 is shown attached to tibia 33 in a less than optimal position. In practice, anchor 3 is preferably attached to tibia 33 slightly medial relative to the illustrated point of attachment.

Femur 31 and tibia 33 are shown. Tibia 33 has been prepared for the placement of the device by the drilling of bone tunnel 37. Adjustable connector 1 and fixed connector 39 (a titanium alloy bobbin in this illustration), have both been attached to bone on opposite sides of the joint by bone screws 41. A length of prosthetic ligament 43, which has in this illustration a loop on each end, is engaged with the body of the fixed connector and to ring 29 of adjustable connector 1.

In the placement of adjustable connector 1 in bone tunnel 37, flutes 27 on cylinder 7 have imparted and/or engaged matching recesses in the wall of bone tunnel 37. Thus when pin 5 is rotated, cylinder 7 cannot rotate with it, but must move axially along the bone tunnel, thus varying the tension on prosthetic ligament 43. It is notable that this embodiment of the device allows continuous, as opposed to incremental, adjustment of tension. Also, it is contemplated that this embodiment of the device can afford relatively easy adjustment of tension if such adjustment becomes necessary after a period of use. Since head 15 of pin 5 is on the tibia, a small incision exposing head 15 can allow adjustment of tension in a relatively minor subsequent surgical procedure.

Other embodiments consistent with the general principle of a connector comprising an axially adjustable member adapted to engage an anchor and a prosthetic ligament are contemplated. For example, an embodiment wherein the adjustable member is a cylinder with a threaded bone therein and having a rounded head capable of swivel movement within a complementary rounded socket in an anchor, and wherein a complementary threaded pin has a means such as a ring or a hook for engaging a prosthetic ligament, can be used in a manner analogous to the embodiment of FIGS. 1 and 2. Likewise, well known means other than a threaded bore and a complementary threaded pin can be used to achieve axial adjustability.

Figure 3:
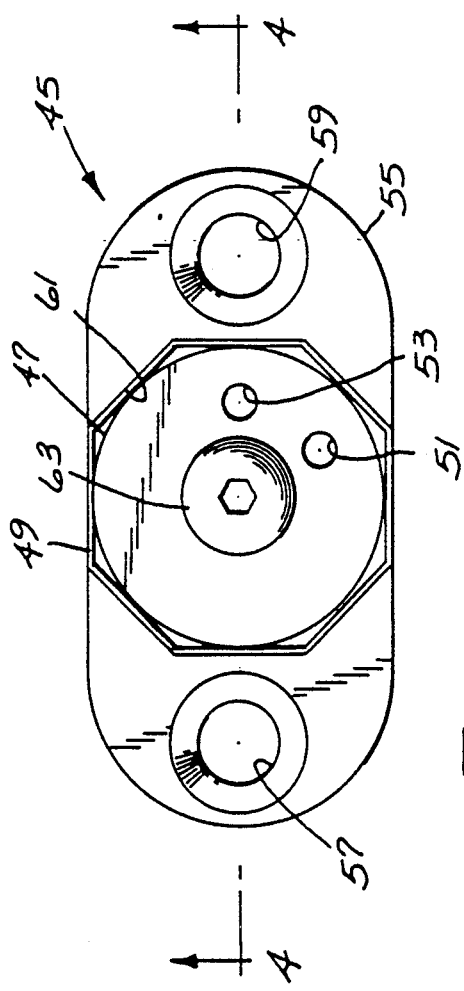
FIG. 3 is a top view of an adjustable connector for use in a device of the present invention, wherein the adjustable aspect arises from a spool with a ratchet plate operating in conjunction with an attachment plate.

FIG. 3 is a top view of a second embodiment of the adjustable connector for use in a device of the present invention, wherein the adjustable aspect arises from a spool with a ratchet plate operating in conjunction with an attachment plate. In this embodiment, adjustable connector 45 comprises spool 47 having ratchet plate 49 attached to the lower side. Means for engaging a prosthetic ligament are needed, and the illustrated variation has loop holes 51 and 53 to provide this function.

Spool 47 operates in conjunction with attachment plate 55, which is adapted to be attached to living bone, e.g., via bone screws passing through screw holes 57 and 59. The attachment plate also has mating surface 61 adapted to engage ratchet plate 49 on spool 47. In the illustration here, ratchet plate 49 comprises a polygonal plate and mating surface 61 is a polygonal recess that is sized to receive the polygonal plate. Toothed ratchets and other forms of ratchets are also contemplated within the scope of the present invention, but the illustrated embodiment is preferred because it presents the lowest vertical height off the bone so that irritation of nearby structures is minimized.

Fastening means for fastening spool 47 to attachment plate 55 is required. Fastening means preferably have a partially engaged position and a fully engaged position, such that in the partially engaged position, the spool can be rotated to adjust the tension on the prosthetic ligament, but when in the fully engaged position the spool cannot rotate. In the illustrated embodiment, means for fastening comprise holding screw 63, which engages a threaded hole in attachment plate 55. When holding screw 63 is partially loosened, ratchet plate 49 can lift up off mating surface 61 and be rotated freely. When holding screw 63 is fully tightened, ratchet plate 49 is in firm engagement with mating surface 61 and rotation is no longer possible.

Figure 4:
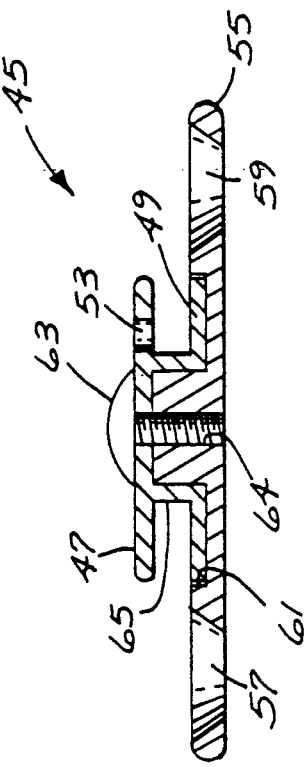
FIG. 4 is a side view of the adjustable connector illustrated in FIG. 3.

FIG. 4 is a side view of the adjustable connector shown in in FIG. 3. In this view, mating surface 61 is partially seen at the central edge of attachment plate 55. Also it will be seen that holding screw 63 engages threaded retaining hole 64 in attachment plate 55. When holding screw 63 is turned partially out from retaining hole 64, ratchet plate 49 can lift up off mating surface 61 and rotate freely. When holding screw 63 is fully tightened into the retaining hole, ratchet plate 49 is in firm engagement with mating surface 61 and rotation is no longer possible.

In this view, spool 47 is seen to include winding shaft 65 around which the prosthetic ligament will be wound in order to take up tension. Turning the ratchet plate allows for incremental adjustment of tension. The increments, however, are relatively small since the ratchet plate need be turned only 360/n degrees (where n is the number of sides of the polygonal ratchet plate and mating surface) between increments, and the winding shaft is of relatively small diameter.

Figure 5:
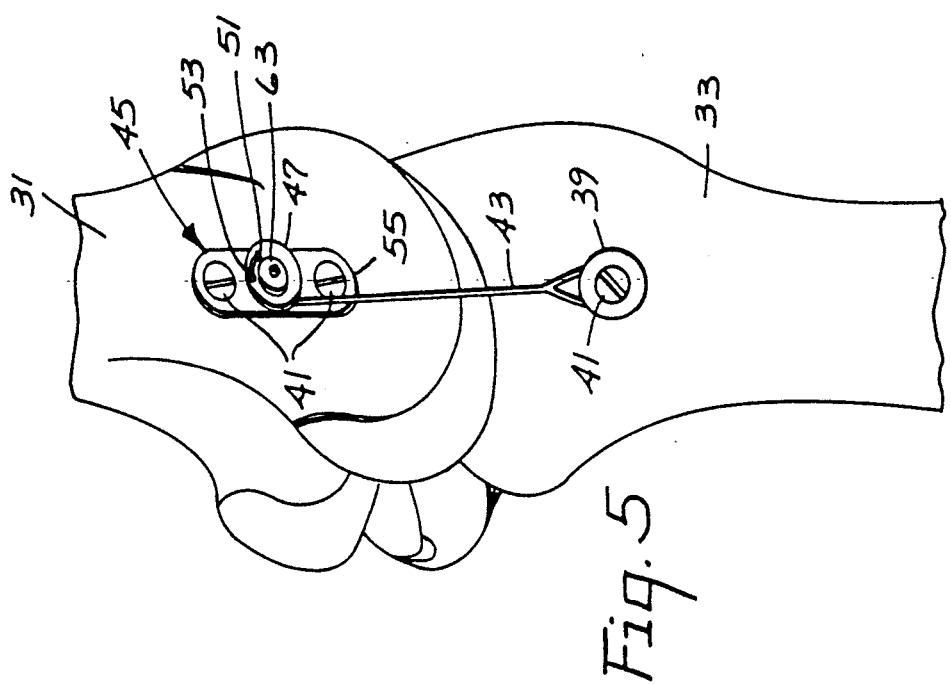
FIG. 5 is a side view of a human knee joint showing a device of the invention comprising a fixed connector and the adjustable connector illustrated in FIG. 3 in place with a prosthetic ligament attached, thus forming a prosthesis for a collateral ligament.

FIG. 5 is a side view of a human knee joint showing a device of the invention comprising a fixed connector and the adjustable connector of FIG. 3 in place with a prosthetic ligament engaged with both, thus forming a prosthesis for a collateral ligament. Adjustable connector 45 of this embodiment has been attached to human femur 31 using a pair of bone screws 41. Fixed connector 39 has been attached to tibia 33 on the opposite side of the knee joint from adjustable connector 45. Prosthetic ligament 43 has been positioned between the fixed connector and the adjustable connector and engages them both. This engagement is provided at the adjustable connector via loop holes 51 and 53 in spool 47. Tension has been taken on prosthetic ligament 43 by turning spool 47, wrapping prosthetic ligament 43 about shaft 65 (not seen in this view) of spool 47. In this illustration, spool 47 is seen in its fully engaged position, its ratchet plate held immobile against the mating surface in attachment plate 55 by holding screw 63.

FIG. 6 is a top view of a third embodiment of the adjustable connector for use in a device of the present invention, wherein the adjustable aspect arises from a cleat plate with multiple cleats for variable engagement with the prosthetic ligament. In this embodiment, adjustable connector 66 comprises cleat plate 67 adapted to be attached to living bone through bone screws passing through screw holes 69. Several cleats 71 are mounted on cleat plate 67 and adapted to engage the prosthetic ligament, for example by having a loop in the end of the prosthetic ligament, which loop slips over the top of a cleat.

It is notable that there exist a plurality of routes around the illustrated cleats for routing the prosthetic ligament leading to the point of engagement between one of the cleats and the prosthetic ligament, each route having a different path length and hence causing a different tension on the prosthetic ligament. While adjustment in this embodiment is incremental, the increments of adjustment are again quite small.

In order to provide a consistent point of departure from cleat plate 67 for the prosthetic ligament as the surgeon tries different paths, guide hole 73 is provided at one end of cleat plate 67 through which the prosthetic ligament passes.

FIG. 7 is a side view of the adjustable connector of FIG. 6. This view emphasizes that cleats 71 can have different orientations to allow the surgeon several ways to route the prosthetic ligament.

FIG. 8 is a side view of a human knee joint showing a device comprising a fixed connector and the adjustable connector of FIG. 6 in place with a prosthetic ligament engaged with both, thus forming a prosthesis for a collateral ligament. Adjustable connector 66 of this embodiment has been attached to human femur 31 using a pair of bone screws 41. Fixed connector 39 has been attached to tibia 33 on the opposite side of the knee joint from adjustable connector 66. Prosthetic ligament 43 has been positioned between the fixed connector and the adjustable connector and engages them both. Engagement is provided at the adjustable connector by passing the prosthetic ligament through guide hole 73, around some of the cleats 71 as appropriate, and then looping it over the top of one of the cleats.

Preferably the adjustable and the fixed connectors are fabricated from titanium alloy, most preferably type Ti-6Al-4V (available from Timet Co., Pittsburgh, Pa.).

Figure 9:
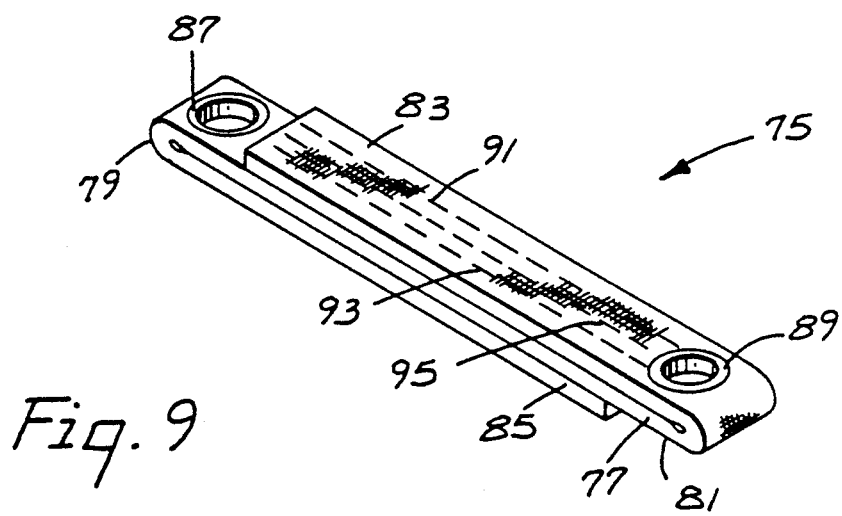
FIG. 9 is a top perspective view of a preferred prosthetic ligament for use in the invention.

The prosthetic ligament can be made of any one of a number of different materials, such as braided fiber ropes of a polyolefin, such as polyethylene or polypropylene, or a polyester. It is contemplated that a flat polypropylene braid with a sacrificial layer, as described in commonly assigned U.S. Ser. No. 214,699, filed July 1, 1988, the disclosure of which is incorporated herein by reference, would be preferred, particularly for use with the embodiments shown in FIGS. 1 and 2 and FIGS. 6–8. Such a prosthetic ligament is illustrated in FIG. 9. In ligament 75 shown in FIG. 9, a unitary strap-like material is used to form load-bearing strap-like element 77, loops 79 and 81 and sacrificial layers 83 and 85. Strap-like element 77, which is the principal load-bearing element of ligament 75, is sandwiched between protective layers having sacrificial areas 83 and 85. Layers 83 and 85 shield load-bearing strap-like element 77 from excessive abrasion at the sites where the ligament contacts bone. In particular, a portion of sacrificial layer 83 extending from approximately the midpoint between eyelets 87 and 89 to near eyelet 87 is positioned between strap-like element 77 and the bone site that element 77 would otherwise contact during use. Similarly, a portion of sacrificial layer 85 from about the midpoint of ligament 75 to the end of sacrificial layer 85 near eyelet 89 protects strap-like element 77 from abrasion at another bone site that element 77 would otherwise contact during use.

Sacrificial layers 83 and 85 are connected or bonded to strap like element 77. In the preferred embodiment illustrated in FIG. 9, three lines of parallel sewn stitches 91, 93, and 95 bond together strap-like element 77 and sacrificial layers 83 and 85.

Loops 79 and 81 provide additional strength to ligament 75 because eyelets 87 and 89 extend through two layers of material that are folded over to provide continuous fibers at the ends of the device.

For use with the embodiments shown in FIGS. 3–5, however, it is contemplated that a cylindrical tubular braid would be preferred, particularly such a braid wherein the ends are of a lesser cross-sectional dimension than the rest of the braid.

The invention is further described in the Examples set forth below.

EXAMPLE 1

A device according to the present invention, comprising an adjustable connector of the type illustrated in FIG. 1, was prepared. The three main parts of this embodiment of the adjustable connector, the anchor, the pin, and the cylinder, were all fabricated from type Ti-6Al-4V titanium alloy (available from Timet, Co.). The socket within the anchor had a spherical radius of 0.1563 inch (0.3969 cm), the centerline of the hole at the base of the socket was canted at a 45 degree angle to the plane of the flange. The rounded head of the pin had a spherical radius of 156 inch (0.40 cm). The threaded end of the pin had a #12-28 male thread, matched by the complementary female thread in the threaded bore of the cylinder.

The cylinder had a maximum outside radius of 0.25 inch (0.64 cm); there were eight flutes on the outside of this cylinder, formed by milling 0.094 inch (0.24 cm) radius troughs longitudinally along the outside surface of the body of the cylinder.

The fixed connector was a simple cylindrical bobbin with a trough along its circumference for capturing a loop in the prosthetic ligament. This bobbin was fabricated from type Ti-6Al-4V titanium alloy (available from Timet, Co.). The prosthetic ligament was fabricated as described in Example 3 below from Spectra 1000 ® brand polyethylene fiber (commercially available from Allied Chemical Corp., Petersburg, Va.).

EXAMPLE 2

The device of Example 1 was implanted into a human cadaver to replace an injured anterior cruciate ligament. The surgery involved the creation of a bone tunnel in the proximal tibia oriented toward the center of the knee joint for the placement of the adjustable connector. The prosthetic ligament was then routed from the adjustable connector over the top of the lateral femoral condyle. The bobbin used as the fixed connector was attached to the lateral distal femur using a bone screw. The adjustable connector was fixed to the tibia generally as depicted in FIG. 2, and one end of the prosthetic ligament was connected to the fixed connector by placing an end loop in the trough around the circumference of the fixed connector. The other end of the prosthetic ligament was connected to the adjustable connector by placing the means for engaging the prosthetic ligament, in this case a hook-like member, of the adjustable connector through the other end loop of the prosthetic ligament. The tension carried by the prosthetic ligament was adjusted by turning the pin in the adjustable connector using a screwdriver in the slot. The tension was increased slowly until the appropriate joint stability was achieved without inhibiting the range of motion.

EXAMPLE 3

A diamond tubular braid was made with 24 tows of Spectra 1000 ® brand polyethylene fiber on a 12 carrier braider (2 tows per carrier). A 25 cm length of braid was used to prepare a prosthetic ligament. To form a loop at each end of the braid, each end of the braid was independently folded back and tucked into an aperture between the loosely braided tows of the tubular braid at a distance of 8.5 cm from the end of the braid. This is a common structure useful for bearing tensile loads. Under a tensile load, the braided tows between which the end of the braid was tucked constrict on the tucked-in end of the braid with sufficient force to keep the tucked-in ends in place, thus maintaining the loops. To provide additional integrity under the dynamic loads encountered by a prosthetic ligament, the tucked-in ends were brought together inside the braid, overlapped 3 cm in the middle of the braid, and sewn together. The final prosthetic ligament had an overall length of 10 cm with a loop 2 cm in diameter at each end. The prosthetic ligament had a tensile strength of 4500N and a stiffness of 2000N/mm.

EXAMPLE 4

An abrasion resistant ligament generally of the type shown in FIG. 9 was made as a flat braid constructed from bundles of polypropylene filaments. The filaments were formed by die extrusion of a polypropylene resin into a bundle of 180 filaments, each filament being approximately 35 microns in diameter. The filament bundle had a tenacity of greater than 7.5 grams per denier.

The flat braid was then fabricated in an 8 mm width containing 13 bundles of filaments. The braid thickness was approximately 1.5 mm.

The prosthetic ligament was constructed, in accordance with FIG. 9, by folding the braid into three layers and sewing the layers together using polypropylene thread. At the end of the sewing area, the braid was cut and heat sealed to prevent unraveling. Using this procedure, end loops 79 and 81 were formed, one at each end of the prosthetic ligament as shown in FIG. 9. The strength of the prosthetic ligament was determined to be about 3300N using the loop ends for tensile loading. In this particular example, eyelets 87 and 89, shown in FIG. 9 were not provided.

It is preferred, however, to provide the eyelets to facilitate attachment of the prosthetic ligament to the connectors. For example, the adjustable connector can be connected to such a prosthetic ligament by guiding a hook-like member on the adjustable connector through an eyelet, and a fixed connector can be placed through the opposite eyelet and then attached to bone. In an embodiment of the prosthetic ligament without an eyelet on the end intended to engage the adjustable connector, a hook-like member on the adjustable connector can be guided through the end loop.

While certain embodiments of the present invention have been described in detail and shown in the accompanying drawing, it will be evident to those skilled in the art that various further modifications are possible without departing from the scope of the invention.

We claim:

1. A device for surgical replacement of ligament, comprising:
   a prosthetic ligament;
   a fixed connector adapted to be attached to living bone and adapted to engage the prosthetic ligament; and
   an adjustable connector adapted to be attached to living bone and adapted to engage the prosthetic ligament; wherein
   when the fixed connector and the adjustable connector are fixed into position and the prosthetic ligament is positioned therebetween and engaged with both, the tension on the prosthetic ligament can be increased or decreased without disturbing the attachment of the device to the bone, and without removal of the prosthetic ligament from either of the connectors,
   wherein the adjustable connector comprises:
   an anchor adapted to be attached to living bone and having walls defining a socket;
   a pin comprising a shaft, a head adapted to engage the socket, and a threaded end opposite the head; and
   a cylinder comprising a body, which body (i) has a threaded bore therein, the threaded bore being adapted to engage the threaded end of the pin, and (ii) comprises means for engaging the prosthetic ligament,
   the device being further characterized in that there exists access to the head of the pin to facilitate adjustment of the adjustable connector.

2. A device according to claim 1, wherein the socket and the head are rounded, permitting swivel movement of the pin.

3. A device according to claim 2, wherein the means for engaging the prosthetic ligament is a ring.

4. A device according to claim 3, wherein the body of the cylinder has flutes on its outer surface, which flutes are adapted to impart and/or engage corresponding recesses in a bone tunnel.

5. A device for surgical replacement of ligament, comprising:
   a prosthetic ligament;
   a fixed connector adapted to be attached to living bone and adapted to engage the prosthetic ligament; and
   an adjustable connector adapted to be attached to living bone and adapted to engage the prosthetic ligament; wherein
   when the fixed connector and the adjustable connector are fixed into position and the prosthetic ligament is positioned therebetween and engaged with both, the tension on the prosthetic ligament can be increased or decreased without disturbing the attachment of the device to the bone, and without removal of the prosthetic ligament from either of the connectors,
   wherein the adjustable connector comprises:
   a spool having a ratchet plate attached and having means for engaging the prosthetic ligament;
   an attachment plate adapted to be attached to living bone and having a mating surface adapted to engage the ratchet plate; and
   means for fastening the spool to the attachment plate which means can be either partially or fully engaged; whereby
   when the means for fastening is partially engaged, the spool can be rotated to adjust the tension on the prosthetic ligament, and when the means for fastening is fully engaged the spool cannot rotate.

6. A device according to claim 5 wherein the ratchet plate comprises a polygonal plate and the mating surface is a polygonal recess.

7. A device ligament according to claim 6 wherein the means for fastening is a holding screw.

8. A device for surgical replacement of ligament, comprising:
   a prosthetic ligament;
   a fixed connector adapted to be attached to living bone and adapted to engage the prosthetic ligament; and
   an adjustable connector adapted to be attached to living bone and adapted to engage the prosthetic ligament; wherein
   when the fixed connector and the adjustable connector are fixed into position and the prosthetic ligament is positioned therebetween and engaged with both, the tension on the prosthetic ligament can be increased or decreased without disturbing the attachment of the device to the bone, and without removal of the prosthetic ligament from either of the connectors,
   wherein the adjustable connector comprises:
   a cleat plate adapted to be attached to living bone and having a plurality of cleats thereon, the cleats being adapted to engage the prosthetic ligament, wherein there exist a plurality of routes around the cleats for the prosthetic ligament, leading to a point of engagement between the cleat plate and the prosthetic ligament, each route having a different path length and hence causing a different tension on the prosthetic ligament.

9. A device as in claim 8 wherein the cleat plate further comprises a guide hole.

10. A kit for use in the surgical replacement of a ligament comprising a prosthetic ligament and an adjustable connector adapted to be attached to living bone and to engage one end of the prosthetic ligament,
    wherein the adjustable connector comprises:
    an anchor adapted to be attached to living bone and having walls defining a socket;

a pin comprising a shaft, a head adapted to engage the socket, and a threaded end opposite the head; and a cylinder comprising a body, which body (i) has a threaded bore therein, the threaded bore being adapted to engage the threaded end of the pin, and (ii) comprises means for engaging the prosthetic ligament, the device being further characterized in that there exists access to the head of the pin to facilitate adjustment of the adjustable connector, and wherein the adjustable connector, when attached in position to bone and engaged with one end of the prosthetic ligament and the prosthetic ligament is anchored to bone at the opposite end, permits the tension on the prosthetic ligament to be increased or decreased without disturbing the attachment of the connector to the bone and without removal of the prosthetic ligament from the connector.

11. A kit according to claim 10 further comprising a fixed connector adapted for attachment to living bone and adapted to engage the end of the prosthetic ligament opposite that engaged by the adjustable connector.

12. A connector for adjustably attaching one end of a prosthetic ligament to living bone comprising:

an anchor adapted to be attached to living bone and having walls defining a socket;

a pin comprising a shaft, a head adapted to engage the socket, and a threaded end opposite the head;

a cylinder comprising a body, which body (i) has a threaded bore therein, the threaded bore being adapted to engage the threaded end of the pin, and (ii) comprises a means for engaging the prosthetic ligament;

the connector being further characterized in that there exists access to the head of the pin for adjusting the position of the pin within the threaded bore of the cylinder so that when the connector is engaged with the prosthetic ligament, the tension on the prosthetic ligament can be increased or decreased without disturbing the attachment of the anchor to the bone and without disengaging the prosthetic ligament from the cylinder.

13. A connector according to claim 12, wherein the socket and the head are rounded, permitting swivel movement of the pin.

14. A connector according to claim 13, wherein the means for engaging the prosthetic ligament is a ring.

15. A connector according to claim 14, wherein the body of the cylinder has flutes on its outer surface, which flutes are adapted to impart and/or engage corresponding recesses in a bone tunnel.

16. A connector for adjustably attaching one end of a prosthetic ligament to living bone comprising:

a spool having a ratchet plate attached and having means for engaging the prosthetic ligament;

an attachment plate adapted to be attached to living bone and having a mating surface adapted to engage the ratchet plate; and means for fastening the spool to the attachment plate which means can be either partially or fully engaged; whereby when the means for fastening is partially engaged, the spool can be rotated to adjust the tension on the prosthetic ligament, and when the means for fastening is fully engaged the spool can not rotate.

17. A connector for adjustably attaching one end of a prosthetic ligament to living bone comprising:

a cleat plate adapted to be attached to living bone and having a plurality of cleats thereon, the cleats being adapted to engage the prosthetic ligament, wherein there exists a plurality of routes around the cleats for the prosthetic ligament, leading to a point of engagement between the cleat plate and the prosthetic ligament, each route having a different path length and hence causing a different tension on the prosthetic ligament.

* * * * *

UNITED STATES PATENT AND TRADEMARK OFFICE
CERTIFICATE OF CORRECTION

PATENT NO. : 5,002,574

DATED : March 26, 1991

INVENTOR(S) : May et al.

It is certified that error appears in the above-identified patent and that said Letters Patent is hereby corrected as shown below:

Col. 3, line 26, "drawing" should read --drawings--.

Col. 3, line 41, "side view" should be replaced with --cross-sectional view along line 4-4--.

Col. 7, line 55, "156" should read --.156--.

Col. 9, line 22, "drawing" should read --drawings--.

Signed and Sealed this

First Day of September, 1992

*Attest:*

DOUGLAS B. COMER

*Attesting Officer*     *Acting Commissioner of Patents and Trademarks*